United States Patent [19]

Yamada

[11] Patent Number: 4,640,445

[45] Date of Patent: Feb. 3, 1987

[54] PORTABLE AND WEARABLE INJECTOR OF MINI SIZE

[75] Inventor: Yasuyuki Yamada, Ishikawa, Japan

[73] Assignee: Nikkiso Co., Ltd., Tokyo, Japan

[21] Appl. No.: 683,811

[22] Filed: Dec. 20, 1984

[30] Foreign Application Priority Data

Dec. 22, 1983 [JP] Japan .................................. 58-242364

[51] Int. Cl.$^4$ ........................ B67D 5/42; A61M 37/00
[52] U.S. Cl. .................................. 222/386.5; 604/145
[58] Field of Search ............... 604/131, 140, 141, 143, 604/145; 222/105, 107, 386, 386.5, 389; 184/39

[56] References Cited

U.S. PATENT DOCUMENTS

| Re. 25,279 | 10/1962 | Crockford et al. | 604/143 X |
|---|---|---|---|
| 2,815,152 | 12/1957 | Mills | 222/386.5 |
| 3,023,750 | 3/1962 | Baron | 222/386.5 X |
| 3,115,280 | 12/1963 | Battista | 222/386.5 X |
| 3,430,731 | 3/1969 | Satzinger | 222/386.5 X |
| 4,023,648 | 5/1977 | Orlitzky et al. | 222/389 X |

OTHER PUBLICATIONS

*Behavior Research Methods & Instrumentation,* 12-1976, vol. 8(6), pp. 487–488, "Instrumentation & Techniques", D. H. Vandercar.

Primary Examiner—Joseph J. Rolla
Assistant Examiner—Michael S. Huppert

[57] ABSTRACT

A portable and wearable injector of mini size is disclosed, which may be operated for injection by means of a gas pressure and which is equipped with an injector syringe and a gas-impermeable flexible bag received in the syringe having one open end for injection and the other sealed end. The bag contains therein a gas-generating device for producing a pressure gas for expanding the bag in order to urge an infusion liquid through the open end of the syringe. As the gas-generating device there may be used an electric or chemical device.

2 Claims, 5 Drawing Figures

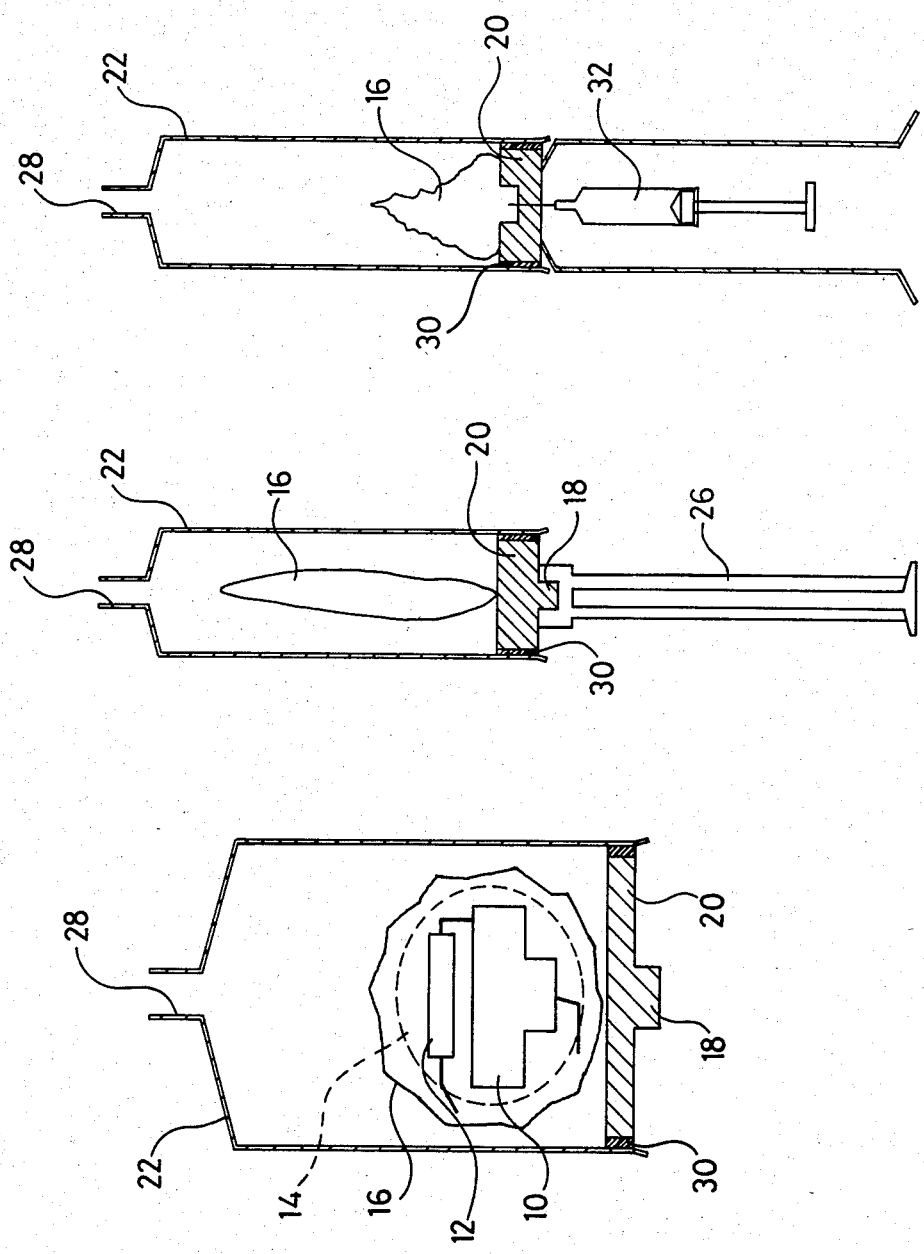

PORTABLE AND WEARABLE INJECTOR OF MINI SIZE

FIELD OF THE INVENTION

This invention relates to a portable and wearable injector of mini size for injecting an infusion liquid, such as a liquid drug, especially by use of a means other than a motor.

BACKGROUND OF THE INVENTION

In the medical and pharmaceutical fields, there has been a need for portable and wearable injector of mini size capable of injecting a small quantity of an infusion liquid, such as a liquid drug, continuously for a long period of time in order to treat diseases, such as cancers, diabetes, sterility, hormonal insufficiency and others. Conventional injectors have utilized a motor as an injecting power source, which makes miniaturization and use of the injectors difficult and inconvenient. Further, such injectors are inconvenient for portability and wearability and very high in cost. In addition, the motor used in the injector requires a relatively large quantity of electric current for driving, which may be supplied only by a large battery.

As injectors of other types without use of the motor, there have been known an injector utilizing a temperature elevation for volumetric expansion or evaporation of a certain substance in the injector syringe to obtain the increased pressure, and an injector utilizing an osmotic pressure. The former injector has a disadvantage of being limited to usage in a specified temperature atmosphere for keeping an injected amount at a constant level, while the latter injector has a problem of inconvenient handling.

Further, the conventional syringe has a large inner cylinder rod for a piston and a grip occupying a half of the syringe volume, which is not usable for the infusion liquid.

Nevertheless, the injection has been carried out intermittently and frequently by means of the conventional types of syringes with the above problems. The intermittent and frequent injections are, of course, troublesome and undesirable for maintaining the proper level of medicine in the blood.

In order to overcome the disadvantages of the conventional injectors as described hereinabove, the inventor has developed and reported a number of microinjectors for injecting the infusion liquid or for protein-analysis [for example, Yamada, Neuroendocrinology 18:263(1975); Yamada, Brain Res. 142:187(1978); Yamada, Endocrinol. Jap. 25:397(1978); Yamada, Brain Res. 172:165 (1979); Yamada, J. Biochem. Biophys. Methods 7:175(1983); Yamada, J. Biochem. Biophys. Methods (in press); Yamada, Proc. Electrophoresis (in press); Yamada, Anal. Biochem. in reform, and others].

It has now been found out that a gas-generating means in an injector may produce a pressure gas within the injector to urge an infusion liquid through a needle attached to one end of the injector, and that an electric or chemical means may be utilized as the gas-generating means. When using the electric means, a generated gas volume by electrolysis of water is directly proportional to an electric current consumed and is 1868 times of volume of water, so that very small quantity of the electric current and very small size of the electric cell are sufficient for the injection purpose.

Accordingly, an object of the invention is to provide a portable and wearable injector of mini-size, which may eliminate the disadvantages of the conventional injectors, such as inconveniently large size, high cost, complicated mechanism requiring a motor with a power source, outer limiting factors (for example, humidity condition), inconvenient handling and others, and which may inject a small quantity of an infusion liquid, such as liquid drug, continuously for long period of time by use of very simple means.

SUMMARY OF THE INVENTION

The above object may be achieved, in accordance with the invention, by a portable and wearable injector which comprises an injector syringe and a gas-impermeable flexible bag received in the syringe, said syringe having one open end for injection and the other sealed end, said bag containing therein a gas-generating means for producing a pressure gas within the syringe to urge an infusion liquid through the open end of the syringe.

As the gas-generating means in the injector according to the invention, there may be used an electric means comprising an aqueous electrolyte and an electric cell for electrolysing the electrolyte thereby to produce the pressure gas within the syringe, or a chemical means comprising at least one reagent, such as hydrogen peroxide and potassium iodide, which may decompose or react with each other to produce the pressure gas within the syringe.

The invention will be described in more detail for better understanding with reference to the accompanying drawings.

BRIEF DESCRIPTION OF THE DRAWINGS

FIG. 1 shows schematic illustration of the injector according to the invention using the electric means as the gas-generating means;

FIGS. 2 and 3 show schematic illustration of the injector according to the invention using the chemical means as the gas-generating means.

PREFERRED EMBODIMENTS OF THE INVENTION

Figure 4:
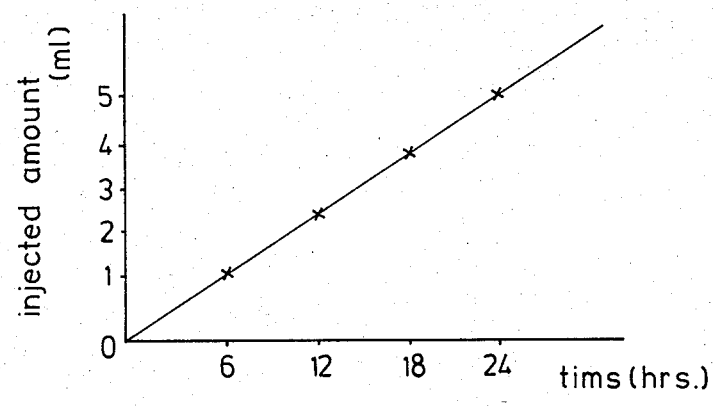
FIGS. 4 and 5 are graphs showing an injected volume of the infusion liquid versus time.

FIG. 1 shows an embodiment of the injector using an electric means as the gas-generating means, in which an injector syringe 22 having one open end 28 for injection and the other sealed end 20 contains therein a gas-impermeable, flexible and collapsible bag 16 which encloses a small electric cell 10 and a serially connected resistor 12 adapted for an injecting quantity of the infusion liquid. The cell 10 and the resistor 12 are provided with respective electrodes wires and coated with an insulating material to form the electric means of a mould type. The electric means is enclosed by a cotton wool 14 which is impregnated with enough amount of an aqueous electrolyte, such as sodium bicarbonate solution. Then, the electric means thus constructed is received in the fexible bag 16 of a size expansible within full space of the injector syringe 22. The bag 16 containing the electric means as the gas-generating means is then collapsed for evacuating air and any gas and received in the injector syringe 22. The electric cell 10 may supply a small quantity of electric current, such as 0.1 mA, depending on the required amount of the pressure gas to be generated within the syringe 22. When the electric current is flowed through the electric means, the gas is generated on a surface of the cotton wool 14, impregnated with an enough amount of the aqueous electrolyte thereby to expand the bag 16 gradually and continuously and thus to urge the infusion liquid, such as liquid drug, through an open end 28 of the syringe 22. Only a very small quantity of water (namely, 1868 part of infusion liquid/1 part of water) is needed to obtain the pressure gas. A motor and its power-transmission mechanism, as well as an inner cylinder rod may be eliminated to provide a half size of the injector, compared with the conventional syringes.

In order to fill the infusion liquid into the syringe 22, the open end 28 is dipped into the infusion liquid and a slidable sealing element 20 (such as a rubber plate or a cylinder) with an engaging element 18 is pulled down by means of a corresponding tool 26 (see, FIG. 2), which may be removed after the filling operation is finished. The sealing element 20 may be made of rubber or provided at its outer circumference with a rubber ring for sealing 30 which may overcome the pressure gas and prevent the sealing element 20 from being pushed down by the pressure gas. If desired, any adhesive may be provided around the sealing portion 30 after placement of the gas-generating means. If the injecting operation is wanted to start on a certain time or intermittently after the filling operation, a commercially available timer IC element of a low price may be incorporated into the electric means as described hereinabove.

When either oxygen or hydrogen should be avoided, a silver electrode wire and any suitable reducing or oxidizing agent may be used in the gas-generating means.

FIGS. 2 and 3 show another embodiment of the injector according to the invention, using a chemical means as the gas-generating means. In accordance with the embodiment, a reactive or decomposable reagent for producing the pressure gas is placed within the bag 16 in lieu of electric means including the cotton wool, while otherwise construction is similar to the embodiment using the electric means. The reagent(s) may be decomposed or reacted with each other to liberate the gas gradually in the bag 16 for expanding the latter, thereby to urge the infusion liquid through the outlet 28 of the syringe 22 in the same way as in the electric means. As the reactive or decomposable reagent for producing the gas, there have been known a number of compounds. Any single compound or a combination of compounds may be used for the purpose of the invention so far as the compound(s) may be decomposed or reacted with each other in a substantially constant decomposition or reaction rate to produce the gas. However, in view of the medical application of the injector according to the invention, non-toxic compound is desirably chosen in a suitable concentration. For this purpose, it has been found out, after screening a number of such compounds, that hydrogen peroxide and potassium iodide are the most preferable combination for the continuous injection of small quantity of the infusion liquid for a long period of time, such as from several hours to 7 or more days. Hydrogen peroxide is well known to react with other compound or to decompose in the presence of a catalyst to liberate oxygen, while potassium iodide may promote the oxygen liberation from hydrogen peroxide. Both hydrogen peroxide and potassium iodide are acceptable for use in the medical application.

When an aqueous solution containing hydrogen peroxide and potassium iodide is used, a larger amount of hydrogen peroxide may increase an injected amount of infusion liquid, while a higher concentration of potassium iodide may increase an injection rate. Thus, the rate, the total period and the total amount of the injection may be readily controlled by the concentration of the reagent(s), depending on purposes of medical treatment. If desired, the injection rate may be controlled by adding another agent, such as a stabilizer or a promoter for the decomposition or reaction.

Of course, it will be appreciated that any shape and structure of the injector other than the conventional syringes may be employed in the invention.

The invention will be described hereinbelow with non-limiting examples for the both embodiments as described hereinabove.

EXAMPLES

Embodiment Using Electric Means

A commercially available electric cell was electrically connected to a commercially available 30 K Ohm resistor to form an electric means of 0.7 cm diameter and about 1 cm length, which was then enclosed in a defatted cotton wool impregnated with adequate amount of Meilon solution (7% $NaHCO_3$ solution, commercially available from Otsuka Pharmaceutical Co., Ltd. Japan). The resulting electrical gas-generating means was received in a gas-impermeable flexible bag of polypropylene, which was then collapsed for evacuating air or any gas in the bag. Then, the collapsed bag containing therein the electrical gas-generating means was placed in a syringe containing 5 ml of a liquid drug, as shown in FIG. 1.

Then, a sufficient electric current was flowed through the electric means for a time required to inject all 5 ml of the liquid drug from the syringe, with the results as follows:

| Elect. Cell | Time Required |
|---|---|
| 1.5 V | (no gas generated) |
| 3.0 V | 24 hours |
| 4.5 V | 1 hour |

Embodiment Using Chemical Means

EXAMPLE 1

0.5 ml of 30% hydrogen peroxide solution, 0.5 ml of 0.01% aqueous potassium iodide solution and 3.5 ml of $H_2O$ were mixed together and 1 ml of the resultant mixture was sealingly put into a plastic flexible bag 16 which had previously been collapsed. The bag thus provided with the reagents was received in a syringe filled with an infusion liquid and then the syringe at its one opening was sealed with a rubber plug 20, while its other opening 28 was left open for injecting the infusion liquid, as shown in FIG. 2. An injected amount of the infusion liquid was determined at a constant interval to obtain the result as shown in FIG. 4. The substantially linear relationship was observed.

EXAMPLE 2

Figure 5:
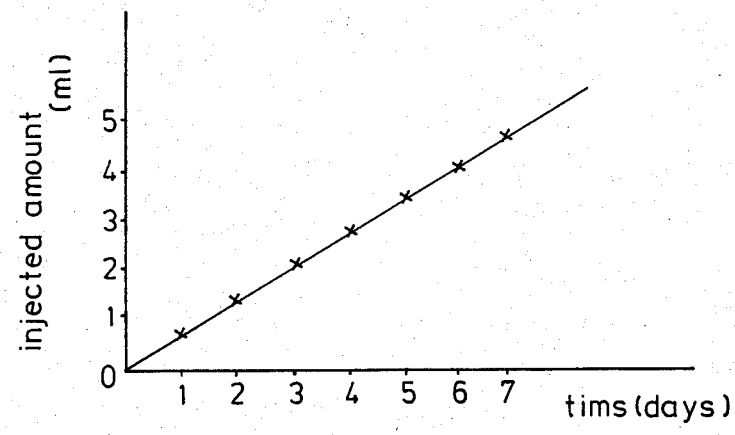

Into a plastic flexible bag 16 containing 2 μg of potassium iodide and previously collapsed in a syringe, as shown in FIG. 3, was introduced 1 ml of 3% hydrogen peroxide solution through a rubber plug 20 by means of a reagent-injecting syringe 32 which was removed after the injection of hydrogen peroxide was completed. Then, the content was well shaken. Thereafter, an infusion liquid was filled in the syringe 22 and an injected amount of the infusion liquid was determined at a constant interval to obtain the result as shown in FIG. 5. The substantially linear relationship was observed between the injected amount and the time elapsed.

Although the invention has been described with the preferred embodiments, many variations and modifications may be made without departing from the scope and sprit of the invention.

What is claimed is:

1. A portable and wearable medical injector of mini size, which comprises an injector syringe and a gas-impermeable flexible bag received in the syringe, said syringe having one open end for injection of an infusion liquid, the other end being sealed, said bag containing therein a gas generating means comprising a chemical substance which is non-toxic to human beings and reactive with hydrogen peroxide, said bag prior to administration of infusion liquid being provided with a predetermined amount of hydrogen peroxide for reaction with the said chemical substance in the bag to produce an oxygen gas in the flexible bag for expanding the bag in the syringe to force the infusion liquid in predetermined quantities and rates over predetermined periods of time out of said open end of the syringe, said syringe being provided with a slidable element which seals its said other end, said slidable element having an extension at its bottom engageable by a tool for pulling the sealing element downwardly for filling the syringe with infusion liquid after mixture of said chemical substance with said hydrogen peroxide.

2. A portable and wearable injector according to claim 1, wherein said chemical substance comprises potassium iodide.

* * * * *